（12）United States Patent
Wynne et al.

(10) Patent No.: US 9,452,074 B2
(45) Date of Patent: Sep. 27, 2016

(54) ORTHOTIC DEVICE AND METHOD

(75) Inventors: James Heffern Wynne, Avon, MA (US); Nate Rand Smiley, Avon, MA (US); Anna Scott, Redruth (GB)

(73) Assignee: DM ORTHOTICS LIMITED (GB)

( * ) Notice: Subject to any disclaimer, the term of this patent is extended or adjusted under 35 U.S.C. 154(b) by 279 days.

(21) Appl. No.: 13/238,653

(22) Filed: Sep. 21, 2011

(65) Prior Publication Data

US 2012/0184887 A1 Jul. 19, 2012

Related U.S. Application Data

(60) Provisional application No. 61/389,733, filed on Oct. 5, 2010.

(51) Int. Cl.
*A61F 5/01* (2006.01)
*A61F 5/02* (2006.01)
*A61F 5/03* (2006.01)

(52) U.S. Cl.
CPC ............ *A61F 5/0111* (2013.01); *A61F 5/0118* (2013.01); *A61F 5/028* (2013.01); *A61F 5/03* (2013.01)

(58) Field of Classification Search
USPC .................. 602/5–6, 12, 19–21, 25–30, 61; 128/845–846; 2/44, 56, 309–311
See application file for complete search history.

(56) References Cited

U.S. PATENT DOCUMENTS

| 3,717,143 | A | * | 2/1973 | Johnson | 602/19 |
|---|---|---|---|---|---|
| 4,593,788 | A | * | 6/1986 | Miller | 182/3 |
| 4,628,913 | A | * | 12/1986 | Lerman | A61F 5/024 602/18 |
| 5,038,760 | A | | 8/1991 | Osborn | |
| 5,256,135 | A | * | 10/1993 | Avihod | 602/19 |
| 5,474,523 | A | | 12/1995 | Miller | |
| 5,733,249 | A | | 3/1998 | Katzin et al. | |
| D417,125 | S | | 11/1999 | Miller | |
| 5,984,886 | A | | 11/1999 | Miller | |
| 6,066,108 | A | * | 5/2000 | Lundberg | A61F 5/028 2/919 |
| 6,364,851 | B1 | * | 4/2002 | Nafpliotis | 602/19 |

FOREIGN PATENT DOCUMENTS

| FR | 2697998 | 5/1994 |
|---|---|---|
| WO | 0053131 | 9/2000 |
| WO | 2006117808 | 11/2006 |
| WO | 2009055873 | 5/2009 |

OTHER PUBLICATIONS

Matthews et al., "Effects of dynamic elastomeric fabric orthoses on children with cerebral palsy," Prosthetics and Orthotics International (2009), vol. 33, No. 4, pp. 339-347.

(Continued)

*Primary Examiner* — Ophelia A Hawthorne
(74) *Attorney, Agent, or Firm* — Gardner Groff Greenwald & Villanueva, P.C.

(57) ABSTRACT

An orthotic device includes a resilient portion configured to apply a force in one or more predetermined directions to assist or restrict movement of a part of a wearer's body, and a rigid portion configured to restrict movement of the body part. The rigid portion is removably-couplable to the resilient portion so that it can be removed from, and coupled to, the resilient portion while the device is being worn.

19 Claims, 11 Drawing Sheets

(56) References Cited

OTHER PUBLICATIONS

Matthews et al., "The use of dynamic Lycra orthosis in the treatment of scoliosis: A case study." Prosthetics and Orthotics International (2006), vol. 30, No. 2, pp. 174-181.
International Search Report for PCT/GB2011/001379, dated Jun. 1, 2012, 10 pages.
International Preliminary Report on Patentability for PCT/GB2011/001379, dated Mar. 26, 2013, 6 pages.
First Examination Report, dated Sep. 19, 2013, 3 pages.
Examination Report for Application No. GB1306960.4, dated Mar. 3, 2014, 3 pages.
Communication Pursuant to Rules 161(1) and 162 EPC for Application No. 11764242.1, dated May 6, 2013, 2 pages.
First Notification of Office Action and Search Report for Application No. 201180054557.8, dated Sep. 23, 2014.

\* cited by examiner

Flexed 45 degrees

Neutral (10 degrees extension)

Pronated (10 degrees)

Ulna deviation
(10 degrees)

ORTHOTIC DEVICE AND METHOD

CROSS-REFERENCE TO RELATED APPLICATION

This application claims the priority benefits of Great Britain Application No. 1015871.5, filed Sep. 21, 2010, and U.S. Provisional Patent Application Ser. No. 61/389,733, filed Oct. 5, 2010, which are hereby incorporated herein by reference.

TECHNICAL FIELD

The invention relates to an orthotic device, in particular an orthotic device for the relief or correction of an orthopaedic or neurological condition. The invention also relates to a method for treating such conditions.

BACKGROUND

Various conditions exist that may inhibit an individual from moving one or more of their body parts in a normal way. Such orthopaedic conditions may be congenital conditions, or may be caused as a result of injury or misuse. For example, cerebral palsy sufferers often exhibit spastic diplegia of varying degrees of severity, which adversely influences the sufferer's ability to walk normally. Treatment and management regimens for spasticity often include the use of orthoses such as splints or braces for discouraging and/or preventing poor postures and undesirable movement of body parts that may cause pain or develop into to greater disability and deformity. For example, orthoses may be employed to enable a sufferer to sit in a normal position, or to hold a sufferer's limbs in advantageous positions to improve functionality of those limbs and prevent deformities.

Scoliosis, a lateral curvature, often coupled with vertebral rotation, of the spine, is an example of an orthopaedic condition that may be treated by an orthotic device. A typical non-surgical treatment of scoliosis involves the use of a rigid thoracic brace to hold the spine in a preferential position, thereby enabling a wearer to experience improved posture and limb functionality. Typically, treatment involves the wearing of a brace for up to 23 hours in a day. Studies have shown that such treatment may have a positive effect when the brace is worn for the prescribed periods of time. However, compliance with the prescribed treatment regimen may often be poor due to the inconvenience of wearing a rigid brace for long periods of time. Studies have shown that in some cases a brace was only worn 20% of the prescribed time, resulting in the treatment having little effect on prognosis of the scoliosis (Howton et al. 1987 orthopaedic transactions 11: 125-126).

A rigid orthotic device such as a thoracic brace used for treatment of scoliosis, or a rigid ankle-foot orthotic device used to ameliorate the effects of spastic diplegia, only has an effect on the patient whilst the device is being worn. When the device is removed the restricted body part reverts to its undesirable condition.

It is an aim of the invention to provide an improved orthotic device and methods of treatment.

SUMMARY

The invention provides an orthotic device, an elastomeric fabric orthosis, and methods of using an orthotic device as defined in the appended independent claims to which reference should now be made. Preferred and/or advantageous features of the invention are set out in various dependent sub-claims.

Thus, a first aspect of the invention may provide an orthotic device comprising a first portion and second portion. The first portion comprises a resilient material for conforming to a portion of a wearer's body and is configured to apply a force in one or more predetermined directions to assist or restrict movement of at least one part of the wearer's body. Preferably, the force is a force for correcting or alleviating an orthopaedic or neurologic condition, particularly preferably a force having sufficient magnitude and acting in a predetermined direction such that it is capable of correcting or alleviating an orthopaedic or neurologic condition. The second portion comprises a rigid, or semi-rigid, material for restricting movement of at least one part of the wearer's body in one or more predetermined directions. The second portion is removably couplable to the first portion such that it can be removed from the first portion, or coupled to the first portion, while the first portion of the orthotic device is being worn by the wearer or patient. The first portion may act to restrict movement in the same direction as the second portion. Alternatively, or in addition, the first portion may act to restrict movement in a different direction to the second portion.

The device is an orthotic device for assisting or restricting movement in at least at least one part of a wearer's body, which may alternatively be described as assisting or restricting movement in at least one joint in a wearer's body. The same device may act to both assist and restrict. For example, in one embodiment the device may be a device for assisting and restricting movement in a wearer's ankle. The first portion may apply a force that promotes, for example, dorsiflexion of the wearer's foot and the second portion may be configured to restrict or prevent plantarflexion of the wearer's foot.

Rigid orthotic devices have been worn in conjunction with garments to improve the comfort of the wearer, or with liners designed to improve comfort and allow sweat to be conveyed away from the wearer's skin. Such liners or garments did not apply a force in one or more predetermined directions to assist or restrict movement of a portion of the wearer's body.

Preferably the first portion comprises a base elastomeric material or underlying elastomeric material that may conform to the wearer's body. The underlying elastomeric material is preferably multidirectionably stretchable, i.e. the underlying material is capable of conforming to the desired portion of the wearer's body but does not generate overall forces, or give rise to lines of tension or compression, in any specific direction. The underlying elastomeric material of the first portion is preferably formed from any such suitable elastomeric material, for example materials comprising a polyurethane-polyurea copolymer such as DORLASTAN®, SPANDEX®, or LYCRA® materials. A particularly suitable material may be a polyamide-cotton-Dorlastan® material, for example a material comprising 51% polyamide, 17% cotton and 32% DORLASTAN® material.

Preferably the first portion further comprises a resilient means for applying a force acting in one or more predetermined directions to assist and/or restrict movement of at least one part of the wearer's body. Particularly preferably, the resilient means comprises one or more strips or panels of resilient material or elastic material that are attached to the base/underlying elastomeric material of the first portion to provide a tension force or compression force to a portion of the wearer's body. For example, the resilient means may be one or more elongated strips or panels of a resilient material such as a nylon/cotton material or a nylon/LYCRA® material, for example a material comprising 81% polyamide and 19% LYCRA® material.

Additional resilient strips or panels may be attached to the first portion so that they overlay existing resilient strips or panels. Thus, reference in this document to attaching resilient means, strips or panels to the first portion of the device includes the attachment of resilient means, strips or panels to a base/underlying elastomeric material, and also to the attachment of a resilient means, strips or panels to a first portion that has existing resilient means, strips or panels attached.

The resilient means, for example one or more resilient strips or panels, may provide a constant force to a portion of the wearer's body that urges that portion of the wearer's body in a specific direction. The resilient means may provide a force that resists movement of the wearer's body when the wearer moves that portion of their body in a specific direction.

In preferred embodiments, panels or strips of resilient material may be attached to the first portion in a non-tensioned condition, i.e. the panels or strips do not have a force applied to them as they are attached to the underlying material and do not exert a force on the underlying material. In this configuration each panel or strip may, when the first portion of the device is worn, apply a resistive force acting in a specific direction when a portion of a wearer's body is moved in a direction that causes the panel or strip to stretch. The force generated by an individual strip or panel is preferably applied to the wearer's body in the direction of a longitudinal axis of the strip or panel. More than one strip or panel may be used in conjunction such that the sum of the forces applied by the strips or panels results in a net force that is applied to the wearer's body in a direction that is not coincident with a longitudinal axis of any one panel or strip.

Advantageously, panels or strips of resilient material may be attached to the first portion such that they become stretched when the first portion is worn by a wearer. Thus, the resilient panels or strips may, once the first portion has been donned by a wearer, provide a continuous force urging a portion of the wearer's body in a predetermined direction.

In some embodiments, one or more strips or panels of resilient material may be attached to the first portion in a pre-tensioned condition, i.e. the panels or strips are stretched and then attached to the underlying material while stretched. In this configuration the panels or strips are able to exert a force on a wearer's body that continually urges the wearer's body in the direction of the applied force. The force generated by a pre-tensioned strip or panel will resist movement of a wearer's body in a direction that causes the strip or panel to stretch further.

A first portion of an orthotic device as described herein may advantageously comprise both tensioned and non-tensioned panels or strips to generate forces that assist or restrict movement of the wearer's body in a predetermined direction.

The force applied by the resilient means, for example a force applied by a resilient strip or panel, is preferably a force that has an orthotic effect on the wearer or a clinical effect on the wearer. For example, the force is preferably a force capable of assisting or restricting movement of a portion of a wearer's body in order to correct or alleviate an orthopaedic or neurologic condition. Thus, it is preferable that the magnitude of the force and the direction the force is applied in is sufficient to straighten or assist the movement of a portion of a wearer's body such that an orthopaedic or neurologic condition is corrected or alleviated. The magnitude or strength of this force may depend on the disability or abnormality the orthotic device is designed to correct, and the portion of the body that the orthotic device is intended to treat. For example, in an orthotic device for encouraging supination of an infant's wrist the force provided by the first portion of the device to achieve this aim may be slight. Alternatively, in an orthotic device for treating scoliosis in an adult patient the force required to straighten the spine may be high. The magnitude of force and the predetermined direction, or directions, in which the force is applied are preferably determined by a medical professional, preferably on a case-by-case basis.

The first portion may itself be a fully functional dynamic elastomeric fabric orthosis or dynamic movement orthosis for providing a functional orthotic effect on a wearer's body. For example, the first portion may, when worn, provide an orthotic effect that preferentially restricts or assists movement in a portion of the wearer's body in order to treat or manage a disability, deformity or weakness. Thus, the first portion may be an elastomeric orthosis for conforming to a wearer's ankle or lower leg or knee or for conforming to the pelvis or torso of a wearer or the shoulder or elbow or wrist and/or one or more fingers or a wearer.

In preferred embodiments the first portion may be a custom designed or bespoke orthosis and may be prepared according to measurements taken by a medical professional.

By conforming to a portion of the wearer's body the first portion of the orthotic device may exert a slight compressive force to the portion of the wearer's body and this force may advantageously increase the wearer's proprioception of that portion of their body. Proprioception may make an important contribution to a patient's unconscious awareness of a portion of their own body. When wearing certain embodiments of the invention, such as an elastomeric orthotic device for conforming to the pelvic region of a wearer, an improved sense of proprioception may improve the stability of a wearer.

Furthermore, by conforming to a portion of the wearer's body the first portion of the orthotic device may be described as adhering to or gripping the skin of the wearer. This may assist in the transfer of any forces from the resilient strips to a patients joint. For example, if the first portion of the orthotic device includes resilient strips of material that act to provide a rotational force on a limb, this force may be more efficiently transferred if the first portion effectively adheres to the skin of the wearer.

Preferably the orthotic device comprises means for coupling the first portion with the second portion. The means for coupling may be incorporated in the first portion or the means for coupling may be incorporated in the second portion. It may be advantageous for the means for coupling to be incorporated in both the first and second portions.

Suitable means for coupling may include a fastener or a strap combined with a fastener. Thus the means for coupling may comprise a strap for holding the second portion relative to the first portion and a fastener for securing the strap, for example a hook and loop fastener, a popper, a button, a zip, a magnetic fastener, or a buckle.

It is preferable that the second portion is carefully positioned at a predetermined orientation with respect to the wearer's body. It may, thus, be advantageous that the orthotic device comprises a means for locating the second portion in a predetermined position with respect to the first portion. Thus, the first portion may conform to a portion of the wearer's body and then the second portion may be located with respect to this first portion and, thus, located with a respect to a portion of the wearer's body. Preferable means for locating the second portion may comprise a pocket or a slit defined in the first portion, in which at least part of the second portion is insertable into the pocket or slit in order to locate the second portion with respect to the first portion.

The means for coupling the first portion to the second portion may include the means for locating the second portion relative to the first portion. Thus, a means for coupling the second portion to the first portion may incorporate a pocket or slit defined within the first portion. The means for coupling may additionally comprise other elements such as loops or straps to secure the second portion relative to the first portion.

Preferably the second portion comprises an orthotic support or brace. Such a brace may be formed from any suitable rigid or semi-rigid material, for example a polymeric material such as polyethylene or polypropylene. Polymeric materials suitable for forming an orthotic brace may include various copolymers of polyethylene and/or polypropylene, modified polyethylenes, and modified polyethylene copolymers. Suitable polymeric materials may also include various thermoplastics, for example polymers that may be deformed into a new shape on application of a certain temperature, for example after immersing in hot water. Suitable polymeric materials may also include resin based cast polymers.

Other suitable materials for the forming of a brace may include composite structures such a glass-fibre composite or a carbon-fibre composite or lightweight metallic alloy materials. Other materials may be used to form an orthotic support or brace and such materials will be apparent to the skilled person.

Preferably the second portion of the orthotic device is shaped to conform to the portion of the wearer's body. For example if the orthotic device is an orthotic device for assisting and/or restricting movement of a wearers foot (i.e. an ankle-foot orthosis or AFO) then the second portion may be a rigid or semi-rigid brace that conforms to a portion of the wearers lower leg and heel and prevents movement of the foot in a predetermined direction, for example the second portion may prevent a wearer from pointing his or her toes.

In preferred embodiments the second portion may be a custom designed or bespoke support or brace and may be prepared according to measurements taken by a medical professional.

The second portion may be formed from more than one rigid or semi-rigid component. For example, it may be advantageous for the second portion to be articulated or hinged so that the portion is capable of flexing in one direction but not flexing in another direction. Hinged and articulated rigid braces are known in the art.

A preferred embodiment of an orthotic device according to the invention may be an ankle-foot orthosis, in which the first portion is an orthotic sock configured to assist or restrict movement of the wearer's foot in one or more predetermined directions and the second portion is a rigid brace for restricting movement of the wearer's foot in one more predetermined directions. The sock may have an upper portion for encircling a lower portion of the wearer's leg and a slit or a pocket may be defined in this upper portion for receiving part of the brace in order to locate the brace relative to the sock.

The first portion may incorporate one or more resilient panels to apply forces in different predetermined directions to the wearer's foot. For example the sock may comprise one or more anterior panels of resilient material extending along a shin portion and an upper foot portion of the sock in order to assist the dorsiflexion of the wearer's foot and simultaneously resist plantarflexion and pronation. The brace may rigidly prevent plantarflexion of the wearer's foot.

A preferred embodiment of an orthotic device according to the invention may be a pelvic orthosis in which the first portion is a pair of orthotic shorts configured to apply a force in a predetermined direction to compress one or more of the pelvic joints, i.e. to restrict movement of parts of the pelvis, and the second portion is a brace for restricting movement of one or more of the pelvic joints.

Preferably the shorts define one or more pockets or slits for receiving part of the brace to locate the brace in position relative to the shorts and thereby relative to the pelvis.

A preferred embodiment of an orthotic device according to the invention may be a spinal orthosis or a thoracic lumbar orthosis in which the first portion is a resilient suit configured to apply a directional force to the wearer's spinal column and the second portion is a brace for restricting movement of the wearer's spinal column. Preferably the suit defines one or more pockets or slits for receiving part of the brace in order to locate the brace relative to the suit.

A preferred embodiment of an orthotic device according to the invention may be a wrist-hand orthosis in which the first portion is a glove configured to assist or restrict movement of the wearer's hand in one or more predetermined directions and the second portion is a brace for restricting movement of the wearer's hand. For example, the first portion may incorporate one or more resilient panels designed to encourage movements such as supination, pronation, wrist extension and/or radial/ulna deviation. Preferably the glove defines one or more slits or pockets for receiving part of the brace to locate the brace relative to the glove.

Thus, it is preferred that the first portion of the orthotic device is a functional resilient or elastomeric orthosis configured to apply a functional orthotic force in one or more predetermined directions to a portion of the wearer's body and that the second portion is a functional rigid or semi-rigid orthosis for resisting movement of at least one portion of the wearer's body. A wearer may be able to wear the first and second portions of the orthotic device in combination in order to restrict movement of a predetermined part of their body in order to improve, for example, posture or limb function, or in order to relieve pain associated with an orthopaedic disorder. When used in this configuration the first portion may advantageously locate the second portion in an optimum position for the functioning of the second portion. The first portion may also, advantageously, increase proprioception of the portion of the wearer's body by applying a compressive force to that portion of the wearer's body.

Rigid braces are efficient at restricting extension or flexion of a joint. However, they are less efficient at restriction rotational movement of a joint as it is difficult to couple the rigid brace to a patient's limb in a manner that restricts rotation without discomfort. An orthotic device as described herein may be advantageous for use with patients requiring a restriction in rotational movement of a joint. As described above, the first portion may grip or adhere to the skin of a wearer or patient. When coupled to a second portion that comprises a rigid brace configured to restrict movement of a joint beyond a particular rotational angle, the first portion may grip the skin sufficiently for the rigid bracing to be effective without excessive patient discomfort. Furthermore, the first portion may comprise resilient strips or panels that act to assist or restrict rotational movement in order to provide the desired rotational correction to the particular joint.

As a specific example, an orthotic device designed for a patient's wrist may be designed to restrict supination of the patient's forearm. This restriction may be achieved simply by the position at which the rigid second portion couples to the dynamic first portion (i.e. the rigid portion is shaped to restrict rotation, and the position at which the second portion couples to the first portion holds the wrist in the desired position relative to the second portion), it may be achieved by the use of resilient panels on the first portion that restrict supination of the forearm, or there may be a combination of both of these aspects. For such situations, the use of a device that couples both dynamic and rigid elements may provide a distinct advantage over a dynamic or rigid device alone.

It may be particularly advantageous that the second, rigid, portion of the device is primarily designed to prevent flexion or extension of a joint beyond a predetermined angle, and the first, dynamic, portion of the device acts to assist or restrict movement of the same joint in other directions than that restricted by the second portion. For clarity, the first portion may also assist or restrict flexion or extension of the joint. Thus, using an orthotic device designed for a wrist as an example, the second portion may be designed to rigidly hold the wrist at a predetermined extension, say 10 degrees. The second portion may incorporate resilient strips that also encourage extention of the wrist, and in addition, the second portion may include resilient strips that encourage the pronation or supination of the patient's forearm and/or resilient strips that encourage the radial deviation or ulna deviation of the wrist.

Advantageously, the second portion may be decoupled from or removed from the first portion. Unlike prior art orthotic devices, removal of the second portion (which preferably functions as an orthotic brace) does not result in the loss of functional orthotic support of the wearer's body. The wearer may remove the second portion in order to provide some comfort and respite from wearing a rigid brace, or in order to perform specific therapeutic exercises. When the second portion is removed the first portion still acts on the wearer's body. Thus, non-compliance with a prescribed regimen of wearing the rigid portion of the device may not be as detrimental to the treatment as in the prior art example of non-compliance.

Recent research into dynamic elastomeric orthoses has indicated that such orthoses may provide a number of beneficial effects not provided by rigid orthoses. In addition to the benefit that may be provided by increased proprioception of a portion of the wearer's body, dynamic elastomeric orthoses may allow a wearer or patient to develop specific muscle control or build up muscle tone in order to counteract orthotic complaints or problems. For example, the use of dynamic elastomeric orthoses in the treatment of scoliosis has indicated that patients may develop the ability to hold their bodies in preferred postures after a period of treatment, even when their dynamic orthosis has been removed. In patients treated by rigid orthoses no such ability is developed due to inactivity of the underlying muscles initiated by the immobile restriction of the spinal brace.

The use of a resilient orthotic device that applies force in one or more predetermined directions may facilitate the development of preferential muscle structures in the body, for example by allowing the wearer to perform suitable exercises while wearing the orthosis.

Furthermore, a dynamic orthoses may influence the wearer by exerting a continuous force or forces to the body portion on which the dynamic orthotic is being worn. Thus, it may be that the first portion of the orthotic device provides a beneficial orthotic effect when worn in combination with the second portion of the device. The second portion, for example, may rigidly prevent movement of a portion of the wearer's body and, simultaneously, the first portion may provide a continuous force or pressure that positively influences the long term recovery of the wearer.

For wearers who are prescribed various exercise regimes to assist management of their condition, or to assist recovery from their condition, an orthotic device according to the invention may advantageously allow the second (rigid or semi-rigid) portion of the device to be decoupled such that the patient can perform exercises whilst wearing only the first (resilient) portion of the device.

A second aspect the invention may provide an elastomeric fabric orthosis configured to apply a force in one or more predetermined directions to assist or restrict movement in at least one part of a wearer's body, or in at least one joint of a wearer's body, in which the fabric orthosis comprises means for locating a rigid or semi-rigid orthosis in position with respect to the dynamic elastomeric fabric orthosis.

Preferably the means for locating the rigid or semi-rigid orthosis comprises one or more slits or pockets for receiving at least a portion of the rigid or semi-rigid orthosis.

Preferably the elastomeric orthoses further comprises coupling means for removably coupling the rigid or semi-rigid orthosis with the elastomeric orthosis. Such coupling means may comprise a fastener, or loops or straps in combination with a fastener. A suitable fastener may be selected from the group comprising a hook and loop fastener, a popper, a zip, a button, a magnetic fastener, and a buckle. Thus, an elastomeric fabric orthosis according to the second aspect of the invention may be a functional elastomeric fabric orthosis that comprises a means for locating a functional rigid or semi-rigid orthosis.

An elastomeric fabric orthosis according to the second aspect of the invention may form the first portion of an orthotic device according to the first aspect of the invention.

A third aspect of the invention may provide a rigid or semi-rigid orthosis adapted to be removably coupled to an elastomeric fabric orthosis. The rigid or semi-rigid orthosis may comprise means for removably coupling the rigid or semi-rigid orthosis to an elastomeric fabric orthosis. The rigid or semi-rigid orthosis may comprise means, such as lugs, for engaging with an elastomeric fabric orthosis in order to locate the rigid or semi-rigid orthosis with respect to the fabric orthosis.

A rigid or semi-rigid orthosis according to the third aspect of the invention may be used a second portion of an orthotic device according to the first aspect of the invention.

A fourth aspect the invention may provide a method of using an orthotic device comprising a first portion and a second portion. The first portion comprises a resilient material for conforming to a portion of the wearer's body and the second portion comprises a rigid or semi-rigid material. A method according to the fourth aspect comprises the steps of donning the first portion of the orthotic device and then coupling the second portion of the orthotic device to the first portion of the orthotic device.

The method may be a convenient method of providing a patient with a rigid orthotic support.

Preferably the method comprises a step of inserting at least a part of the second portion of the orthotic device into a slit or pocket defined in the first portion or the orthotic device to locate the second portion relative to the first portion. The resilient first portion conforms to a portion of the wearer's body and, thus, may provide a convenient means for locating the second portion of the orthotic device in an appropriate position to have a beneficial effect on the wearer Particularly preferably, the method may comprise the step of releasably fastening a strap to couple the second portion to the first portion.

It may be advantageous that the second portion is removably couplable to the first portion. Thus the method may comprise a step in which the second portion is uncoupled from the first portion and removed from the orthotic device after a period of time has passed. This period of time may be a clinically prescribed period of time in which the first portion and the second portion of the orthotic device are worn together in combination. The period of time may, alternatively, be a period of time in which the first portion and the second portion are worn in combination and after which the wearer wishes to remove the rigid second portion.

It may, thus, be advantageous that the first portion of the orthotic device can be worn separately from the second portion of the orthotic device for a period of time. This period of time may also be a clinically prescribed period of time.

The method may further comprise the step of re-coupling the second portion to the first portion.

A fifth aspect of the invention may provide a method of supporting, aligning, or assisting the movement of a movable part of a wearer's or patient's body. The method according to the fifth aspect may comprise the steps of dressing the patient (wearer) in a resilient orthosis configured to apply a force in one or more predetermined directions to assist or restrict movement of the movable part of the patient's body, and coupling a brace formed from a rigid or semi-rigid material for restricting movement of the movable part of the patients body to the resilient orthosis. The resilient orthosis and the brace are worn by the patient, in combination, for a period of time.

The method may further comprise the step of decoupling the brace from the resilient orthosis such that the resilient orthosis is worn by the patient separately from the brace for a period of time.

The method may provide the further step of re-coupling the brace to the resilient orthosis such that the resilient orthosis and the brace are worn in combination for a further period of time. The resilient orthosis and the brace may form, in combination, an orthotic device as described above.

The periods of time in which the resilient orthosis and the brace are worn in combination and the periods of time in which the resilient orthosis is worn separately from the base may be periods of time that are prescribed by a clinician to treat or manage a particular condition.

The method may be of use in many orthopaedic and/or neurological conditions, for example for treating neurological dysfunctions caused as a result of cerebral palsy, strokes, head injuries, multiple sclerosis, and other neurological conditions. As an example, the treatment of hemiplegia, diplegia, or other forms of spasticity may be treated by the use of a combination of a resilient pelvic orthosis with a rigid pelvic brace or by the combination of resilient orthotic socks with a rigid ankle brace. The treatment of hemiplegia, quadriplegia, cerebral vascular accidents, trauma, multiple sclerosis, and Parkinson's disease may involve the use of a resilient orthotic glove in combination with a rigid wrist brace. The treatment of low thoracic muscular tone, hyperkyphosis of the thoracic spine, aspects of cerebral palsy, and neuropathic scoliosis may be treated by the use of a resilient thoracic orthosis in combination with a rigid thoracic brace.

The method of treatment of a specific condition may include instructions that the brace is to be worn in combination with the resilient orthosis for a predetermined proportion of the total time that the resilient orthosis is worn. Thus, it may be specified that the resilient orthosis is worn in combination with the brace for a proportion of 90% of the total time that the resilient orthosis is worn (or other proportions, for example or 80% or 70% of the time).

Advantageously, the predetermined portion of time may be altered as part of a course of treatment. Thus, the method may comprise a treatment regimen in which the resilient orthosis and the brace are worn together in combination for a high proportion of the time at the start of the treatment and this proportion of the time is progressively reduced as the treatment progresses.

The method of treatment may, thus, proceed to a point in which the brace is worn in combination with the resilient orthosis for only a low proportion of the total time that the resilient orthosis is worn, for example less than 10% of the time. The method may ultimately dispense with the use of the brace if the patient progresses sufficiently for the resilient orthosis to be worn without the brace.

DETAILED DESCRIPTION OF EXAMPLE EMBODIMENTS

Figure 1:
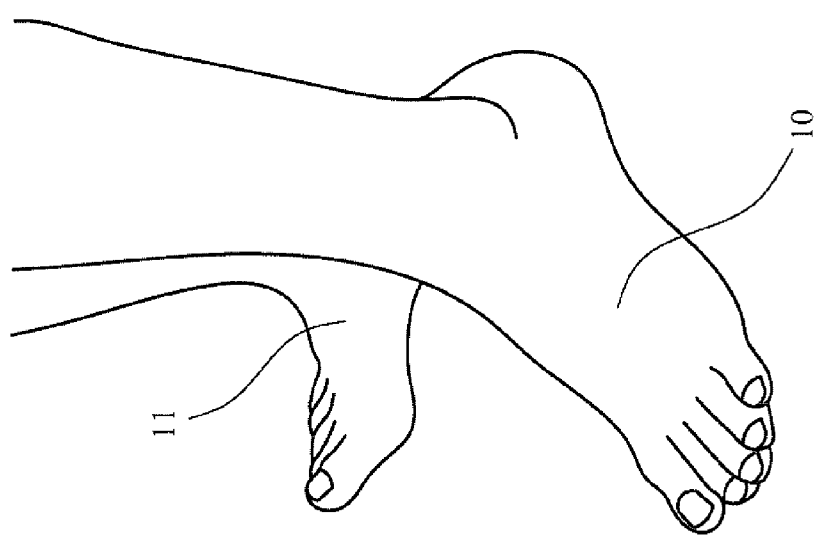
FIG. 1 is an illustration showing the left foot of a hemiplegic patient.
Figure 3:
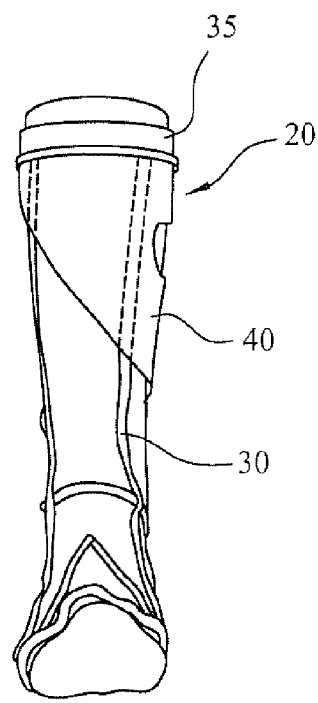
FIG. 3 shows a front view of the orthotic device according to the first embodiment of the invention.
Figure 4:
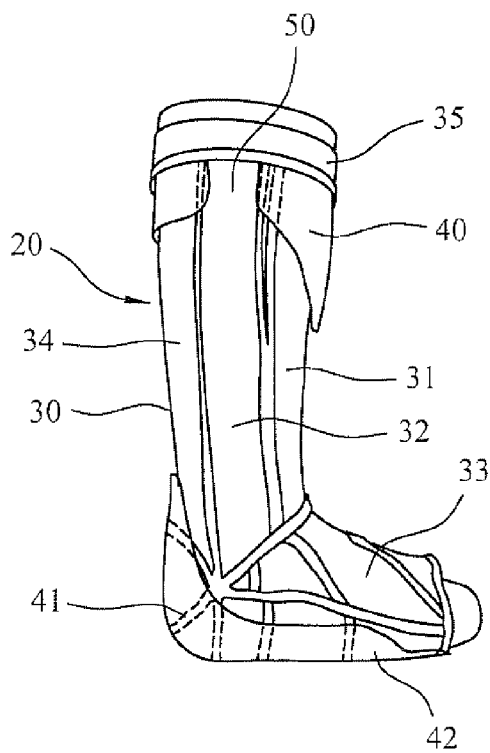
FIG. 4 shows an outside view of the orthotic device according to the first embodiment of the invention.
Figure 5:
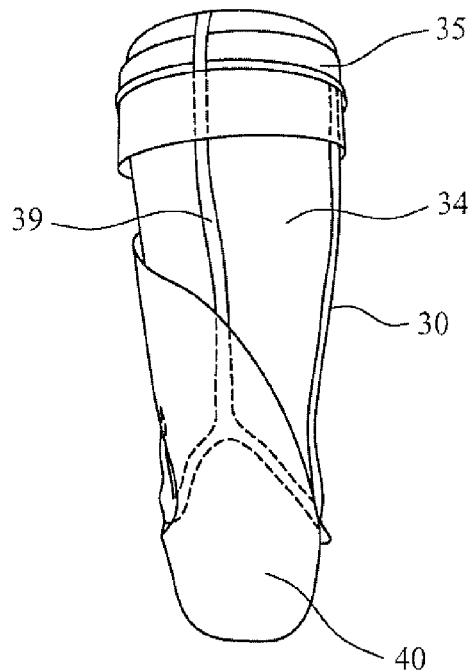
FIG. 5 shows a rear view of the orthotic device according to the first embodiment of the invention.
Figure 6:
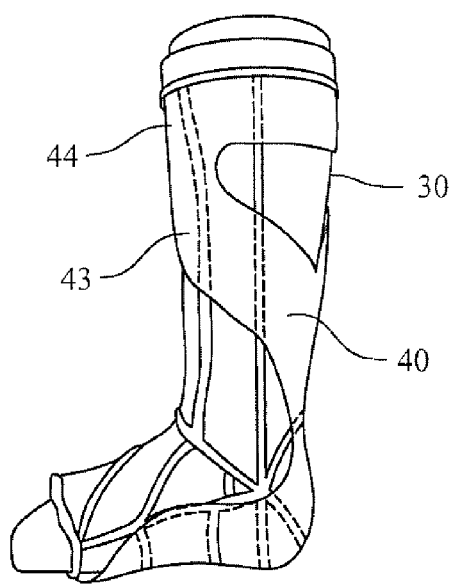
FIG. 6 shows an inside view of the orthotic device according to the first embodiment of the invention.
Figures 7, 8:
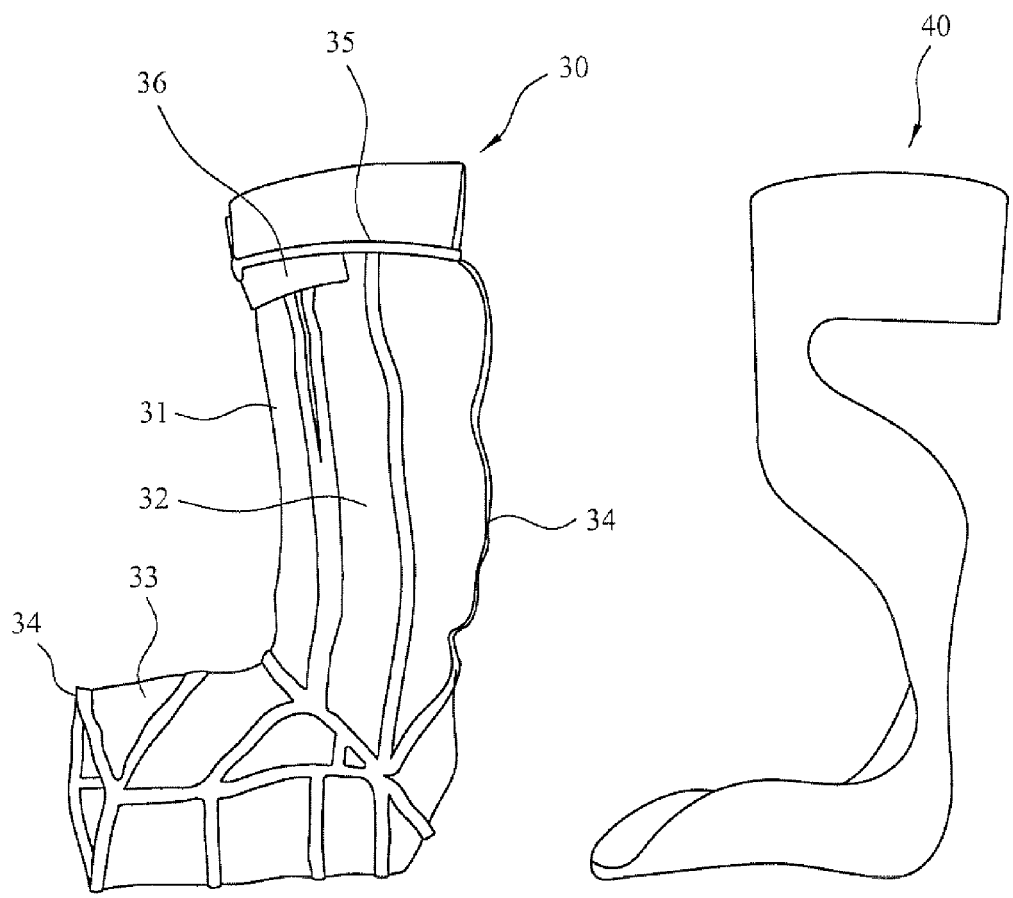
FIG. 7 illustrates an inside view of a first portion of the orthotic device according the first embodiment of the invention.
FIG. 8 shows an inside view of a second portion of the orthotic device according to the first embodiment of the invention.

FIG. 1 illustrates the feet of a hemiplegic patient who is unable to hold their left foot 10 at an angle of 90 degrees relative to their left leg. By comparison, it can be seen that the patient's right foot 11 is capable of being held at 90 degrees relative to their right leg. The inability to hold a foot at 90 degrees may result from a neurological dysfunction which prevents the brain and central nervous system from initiating the foot lifting action (dorsiflexion). Such dysfunction may lead to the patient's toes of their left foot dragging on the ground when they attempt to walk.

Figure 2:
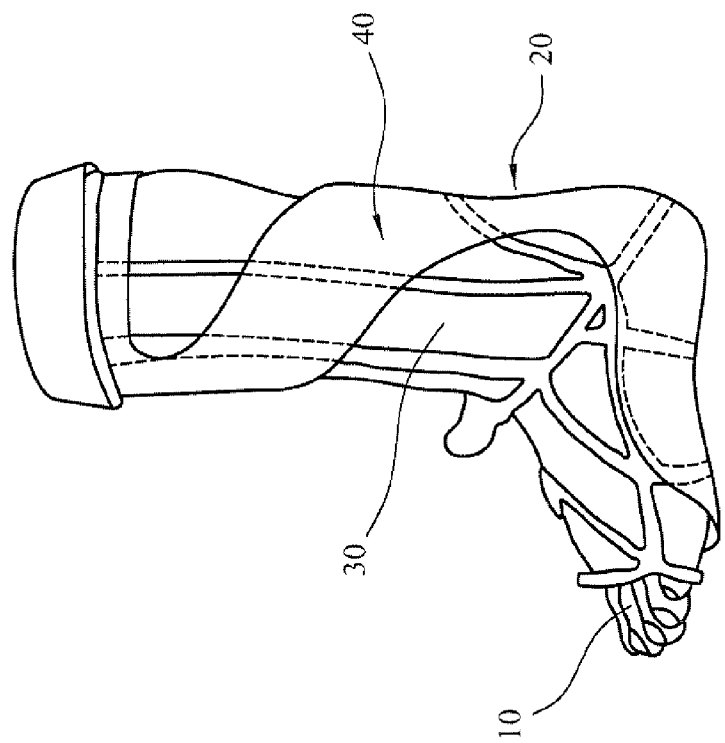
FIG. 2 is an illustration showing the left foot of the patient illustrated in FIG. 1 wearing an ankle-foot orthotic device according to a first embodiment of the invention.

FIG. 2 illustrates the left foot of the same patient wearing an orthotic device 20 according to a first embodiment of the invention comprising two separate couplable portions. The first portion 30 is a dynamic elastomeric orthosis designed to conform to a portion of the patient's foot, ankle and lower leg. The first portion may be described as a sock. The second portion 40 is a rigid polyethylene ankle brace configured to conform to a portion of the patients foot, ankle and lower leg. The elastomeric orthosis first portion 30 and the rigid orthosis second portion 40 are coupled together to form the orthotic device 20.

FIG. 2 shows that the orthotic device holds the patients left foot 10 at an angle of 90 degrees relative to their left leg. In other words, the orthotic device maintains the patient's ankle at a neutral position in which the foot is held at an angle of 90 degrees relative to the leg.

The orthosis or orthotic device 20 of the first embodiment of the invention (as illustrated in FIG. 2) is illustrated in more detail in FIGS. 3 to 8.

The polyethylene ankle brace 40 has a heel portion 41 for conforming to the patient's heel, a foot portion 42 for cradling the sole of the patient's foot, and a leg portion 43 for conforming to at least a portion of the patient's lower leg. An upper portion 44 of the polyethylene brace 40 is configured to substantially encircle a patients leg above the calve muscle or just below the knee joint.

The upper portion 44 of the polyethylene brace 40 does not entirely encircle the patient's leg but incorporates an opening or gap 50 to enable a patient's leg to be inserted into the brace.

The elastomeric orthosis, or sock, 30 is formed from a lightweight breathable elastomeric fabric. Suitable fabrics are readily available, for example fabrics available under the trade names SPANDEX® or LYCRA® may be suitable. In the first embodiment panels of an underlying elastomeric material, having a composition of 51% polyamide, 17% cotton and 32% DORLASTAN® material, are stitched together at seams such as a rear seam 39 in order to define the shape of the sock. The underlying material conforms to the foot, ankle, and lower leg of a wearer, but does not exert any directional forces on the ankle or foot. The sock 30 further comprises a number of elongated resilient dorsiflex-assist panels 31, 32, 33 sewn into the body of the sock over the top of the underlying elastomeric material 34. The dorsiflex assist panels have a composition of 81% polyamide and 19% LYCRA® material, which is an elastomeric material that offers greater resistance to deformation than the underlying elastomeric material.

A pocket 35 is defined at an upper portion of the sock. This pocket is configured to allow the upper portion 44 of the polyethylene brace 40 to be inserted within. The sock 30 further comprises a hook and loop fastener 36 positioned to mate with an opposing hook and loop fastener attached to the polyethylene brace (not shown). The polyethylene brace 40 is, thus, removably coupled to and located relative to the sock 30 by means of the upper portion 44 of the brace 40 being inserted into the pocket 35, wherein a hook and loop fastener 36 prevents the brace 40 from sliding relative to the sock 30.

The upper portion 44 of the brace 40 may comprise a strap for bridging the gap 50. Such a strap may be tightened to further secure the brace to the sock. Such a strap may include hook and loop fasteners (for example VELCRO® fasteners) or may comprise other means such as poppers or buckles. The strap itself may be an elastomeric strap.

In use, a patient first dons the orthotic sock 30 portion of the orthotic device 20. The sock 30 includes dorsiflex-assist panels 31, 32, 33, which may provide a dynamic pull on the foot when the patient flexes his foot. For example, when the patient points his toes, the dorsiflex panels at the shin 31 and foot 33 are stretched. As the panel is stretched, a force is exerted pulling the foot of the patient upwardly towards the shin, pivoting around the heel. Thus the panels assist the dorsiflexion of the foot and resist plantarflexion of the foot.

It is noted that the force that is required to be exerted by the panels in order to assist dorsiflexion and resist plantarflexion will vary from patient to patient and will depend on factors such as the physical size of the patient and the level of their disability. The magnitude of the force may be varied as required in for any specific patient by means such as increasing the number of resilient panels that are aligned to resist dorsiflexion, changing the material that the panels are made form to a material that has a greater resilience, or increasing the thickness of the resilient panels such that they provide greater resilience.

The sock 30 conforms to the patient's foot, ankle and lower leg and is held in position by an elastic upper seam or hem that grips the patient at the top of the calve muscle and below the knee joint.

After the sock portion 30 has been correctly donned, the polyethylene brace 40 is applied. The user squeezes his ankle through the gap 50 defined in the upper portion 44 of the brace 40 and slides his foot down such that the foot and heel are cradled by the foot portion 42 and heel portion 41 of the brace 40. The upper portion 44 of the brace slides into the pocket 35 of the sock 30 and the hook and loop fastener 36 secures the coupling.

The brace 40 prevents the wearer's foot from undergoing any plantarflexion beyond an angle of 90 degrees between the shin and foot. In addition, the sock portion 30 of the orthotic device is exerting a dorsiflexional force on the patient's foot that is continually acting and, thus, the orthotic device 20 acts simultaneously as both a static orthotic device in which the foot is prevented from plantarflexion by the brace 40 and a dynamic orthotic device in which the orthotic sock 30 is continuously exerting a dorsiflexional pull on the patient's foot.

In addition to the dorsiflexion force, the orthotic sock 30 exerts a general all-round compressional force to the wearer's foot, ankle and lower leg. This compression may increase proprioception of the foot, ankle and lower leg and thus assist the wearer in learning muscle control of this portion of the body.

Clinical usage of the orthotic device 20 may specify that the sock portion 30 of the device is worn for a predetermined number of hours per day, for example the sock portion 30 of the device may be required to be worn during a patient's normal active hours of the day. The polyethylene brace portion 40 of the orthotic device 20 may be coupled to, or decoupled from, the sock portion 30 as required by the patient. Alternatively, the rigid brace portion 40 may be coupled to, or decoupled from, the sock portion 30 as directed by a medical professional such as a doctor.

When the rigid brace 40 is decoupled from the sock portion 30 the patient's foot is not rigidly braced and may undergo a certain degree of plantarflexion. By performing exercises or normal activities while the rigid portion is decoupled from the sock portion 30, the patient has the opportunity to build up muscle strength and control in an attempt to improve his clinical condition.

As a patient's foot tires, for example after exercise or after a prolonged period of time with the sock portion being worn individually without the brace, the brace portion may be re-coupled to the sock portion to effect a rigid bracing of the foot and ankle.

It may be advantageous for a patient to increase, over a period of weeks or months, the proportion of each day that they spend wearing the orthotic device 20 with the rigid brace portion 40 decoupled from the orthotic sock portion 30.

Figure 9:
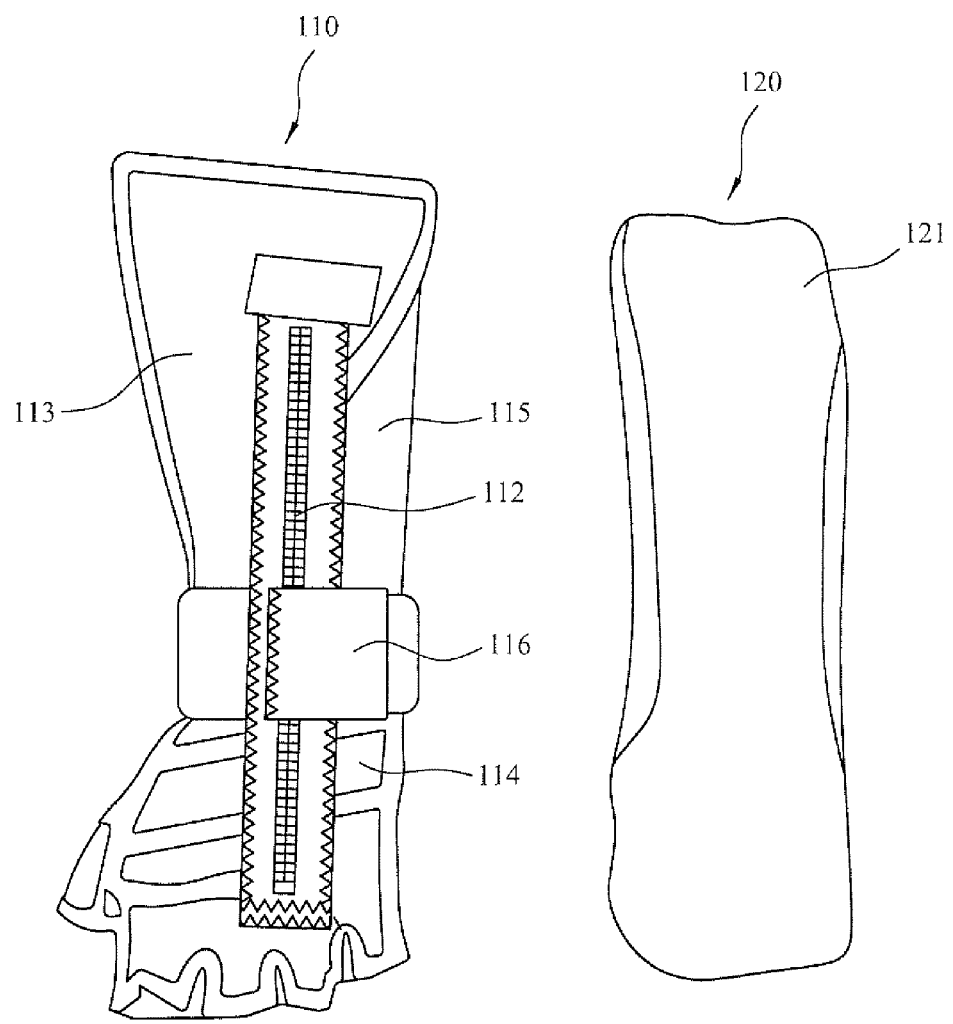
FIG. 9 illustrates a first portion and a second portion of a wrist-hand orthotic device according to a second embodiment of the invention.
Figure 10:
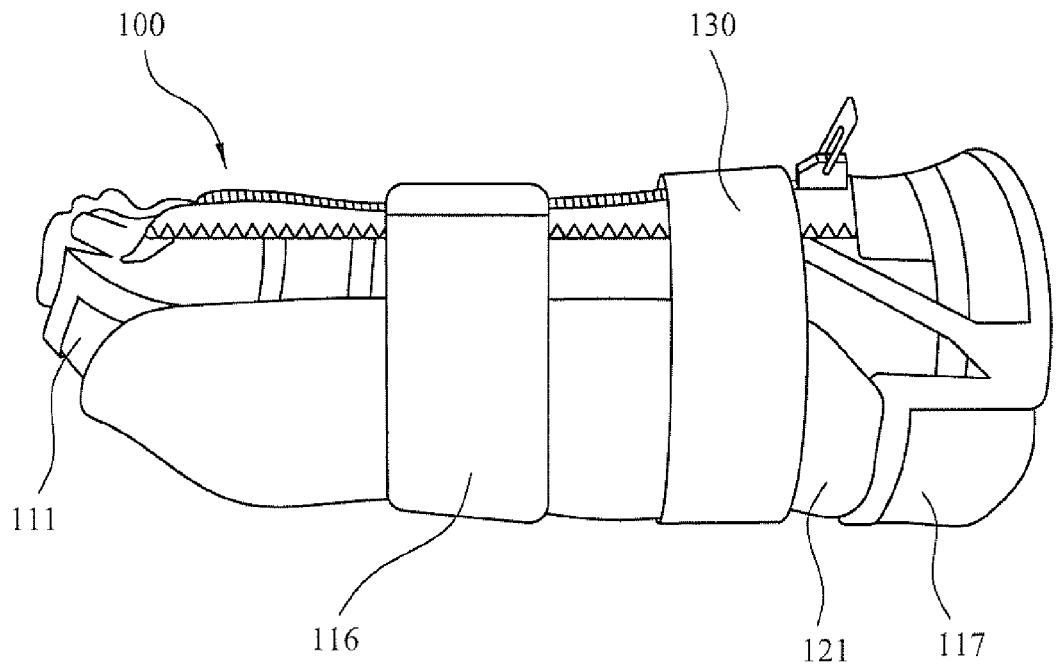
FIG. 10 illustrates a side view of the orthotic device according to the second embodiment of the invention, showing the first portion and the second portion in an as-coupled state.
Figure 11:
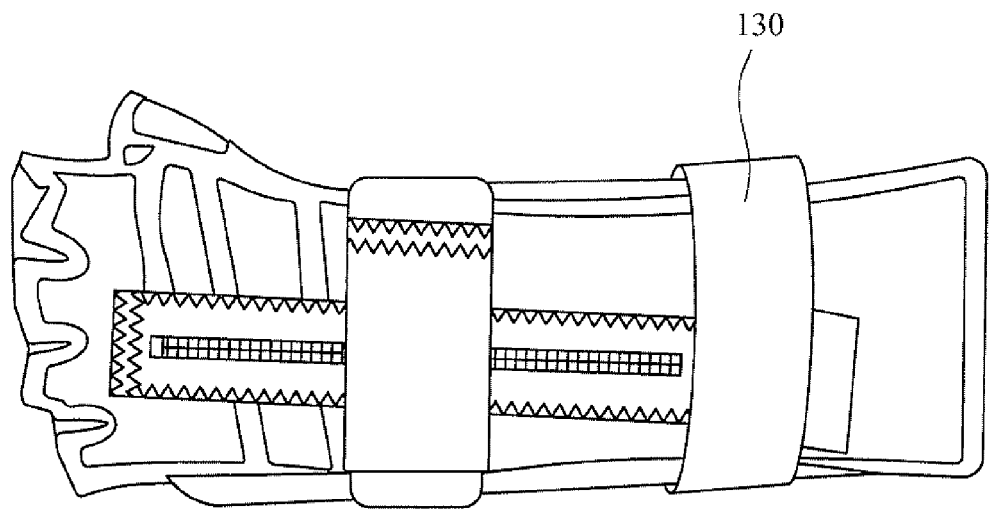
FIG. 11 illustrates a plan view of the orthotic device according to the second embodiment of the invention.

FIGS. 9, 10 and 11 illustrate an orthotic device according to a second embodiment of the invention. These figures show a wrist-hand orthosis or orthotic device 100 comprising two separate couplable portions. The first portion 110 is a dynamic elastomeric orthosis designed to conform to a portion of the patient's hand and wrist, which may be termed a glove. The second portion 120 is a rigid polyethylene wrist brace configured to conform to a portion of the patients wrist. The elastomeric orthosis portion 110 and the rigid orthosis portion 120 are coupled together to form the orthotic device 100.

The elastomeric orthosis 110 is in the form of a glove constructed from a lightweight elastomeric material 111. The glove 110 comprises a zip opening 112 to facilitate donning the glove. Panels of resilient material 113,114, 115 are sewn onto the underlying elastomeric material 111 to apply forces to a wearer's hand and wrist, for example to encourage supination and wrist extension. The underlying material is an elastomeric material having a composition of 51% polyamide, 17% cotton and 32% DORLASTAN® material, and the resilient panels are an elastomeric material having a composition of 81% polyamide and 19% LYCRA® material.

The glove portion 110 further defines a pocket 117 for accepting a portion of the brace portion 120 of the device 100.

The glove portion 110 of the orthotic device 100 further comprises a strap 116 having a hook and loop fastener (a suitable example of which is commercially available as VELCRO® fasteners).

The rigid brace 120 is a custom made polyethylene brace for conforming to the wearer's wrist and lower arm and for supporting the wearer's hand.

In use, a patient unzips the zipper 112 on the glove portion 110 and guides his hand through an opening in the top of the glove. The patient's fingers are then guided through the correct finger openings and the top portion of the glove is pushed along the patient's arm until the glove is correctly positioned. The zipper 112 is then closed.

The patient's wrist is then held at the desired position and the brace portion 120 is moved into position along the lower arm. A top end 121 of the brace 120 is inserted into the pocket 117. With the brace 120 in the correct position, the strap 116 is wrapped around both glove 110 and brace 120 to secure the two portions together. If further securing is required, a further strap 130 may be fastened around both portions.

FIGS. 11A to 11F illustrate the use of the orthotic device as described above in the treatment of a patient who has a condition resulting in abnormal wrist flexion, pronation and ulna deviation.

Figure 11A:
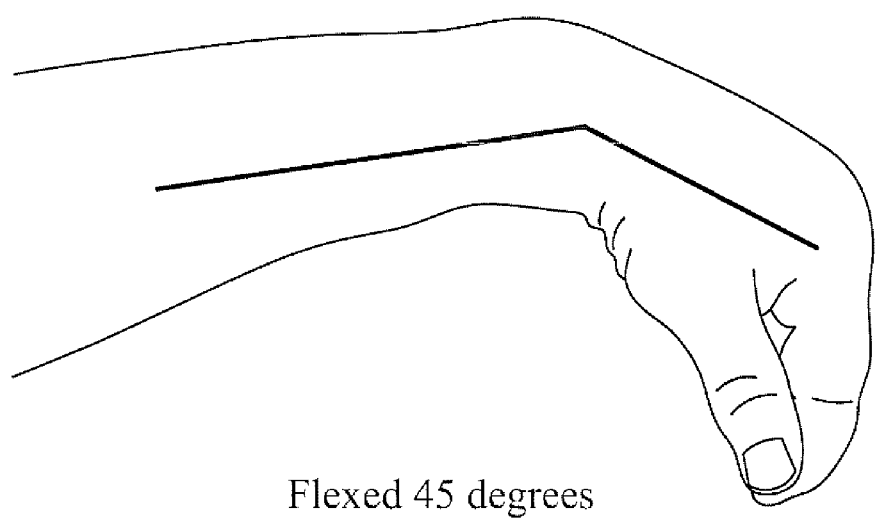
FIGS. 11A and 11B illustrate the use of the device according to the second embodiment of the invention in correcting abnormal flexion of a patient's wrist.
Figure 11B:
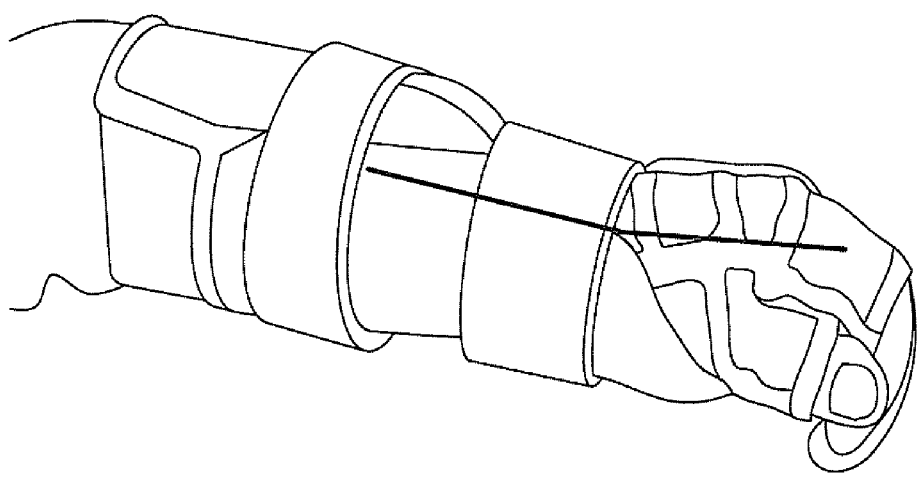

As illustrated in FIG. 11A, the patient's wrist is abnormally flexed at an angle of 45 degrees. The glove 110 includes panels of resilient material that resist the flexion of the wrist and, thereby, reduce the angle at which the wrist is flexed when the glove is worn. When the rigid brace 120 is coupled to the glove 110, as illustrated in FIG. 11B, the patient's wrist is prevented from flexing and is held in a neutral position having 10 degrees of extension. If the rigid brace 120 is de-coupled from the device the wrist may flex once more, but the flexion is resisted by the resilient panels on the glove.

Figure 11C:
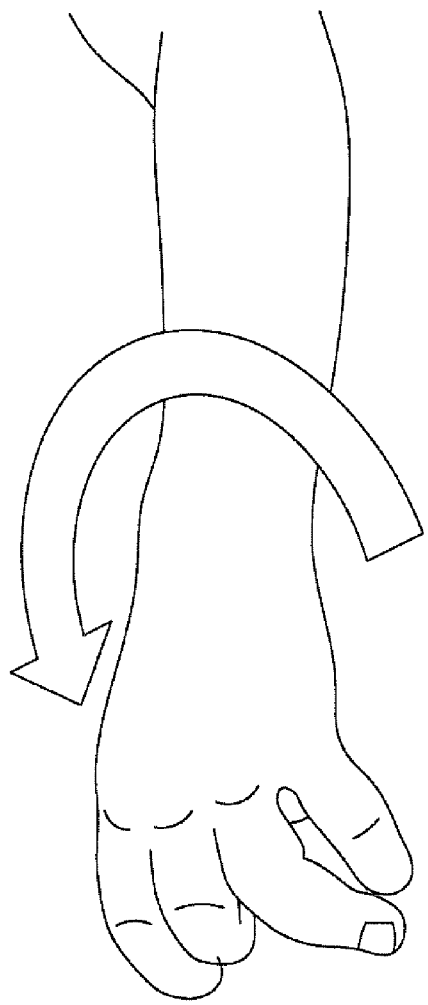
FIGS. 11C and 11D illustrate the use of the device according to the second embodiment of the invention in correcting abnormal pronation of a patient's forearm.
Figure 11D:
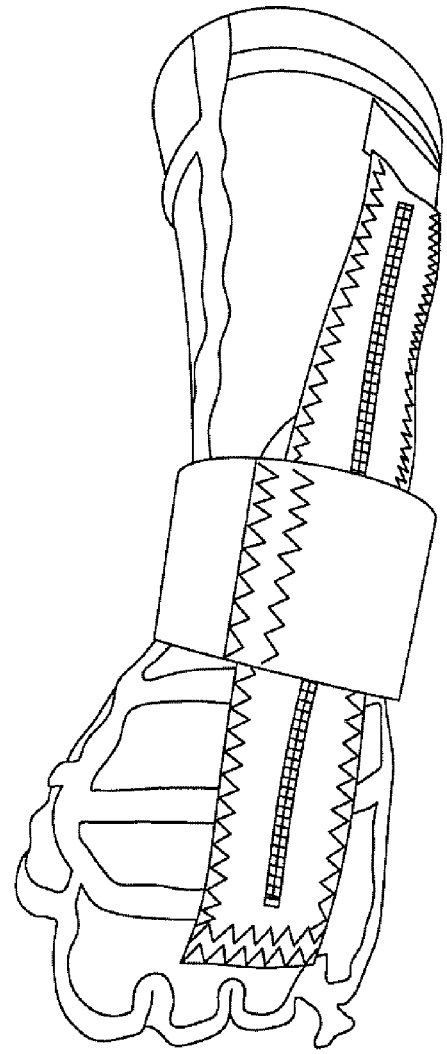

As illustrated in FIG. 11C, the patient's forearm is pronated by an angle of 10 degrees. The resilient panel 115 on the glove 110 applies a twisting force to the forearm to resist this pronation and urge the patient's forearm towards a more neutral position, as illustrated in FIG. 11D.

Figure 11E:
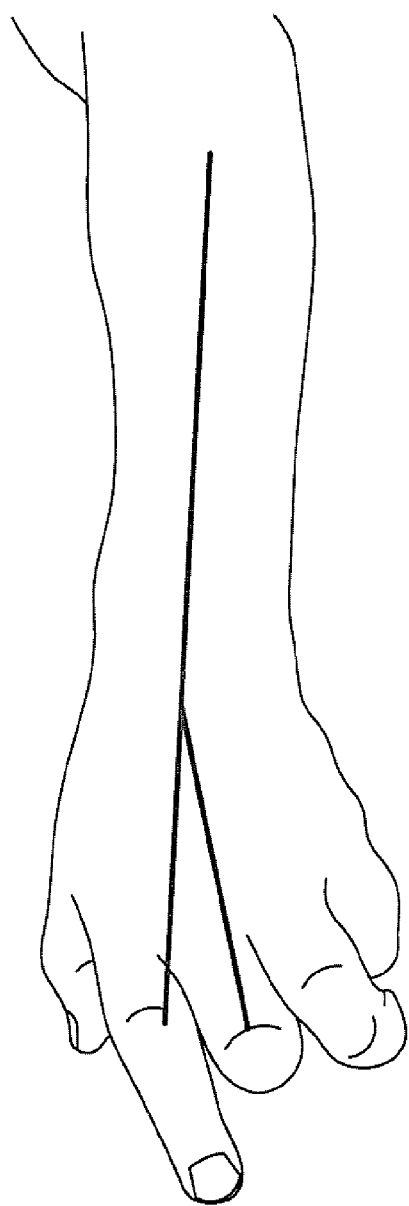
FIGS. 11E and 11F illustrate the use of the device according to the second embodiment of the invention in correcting abnormal ulna deviation in a patient's wrist.
Figure 11F:
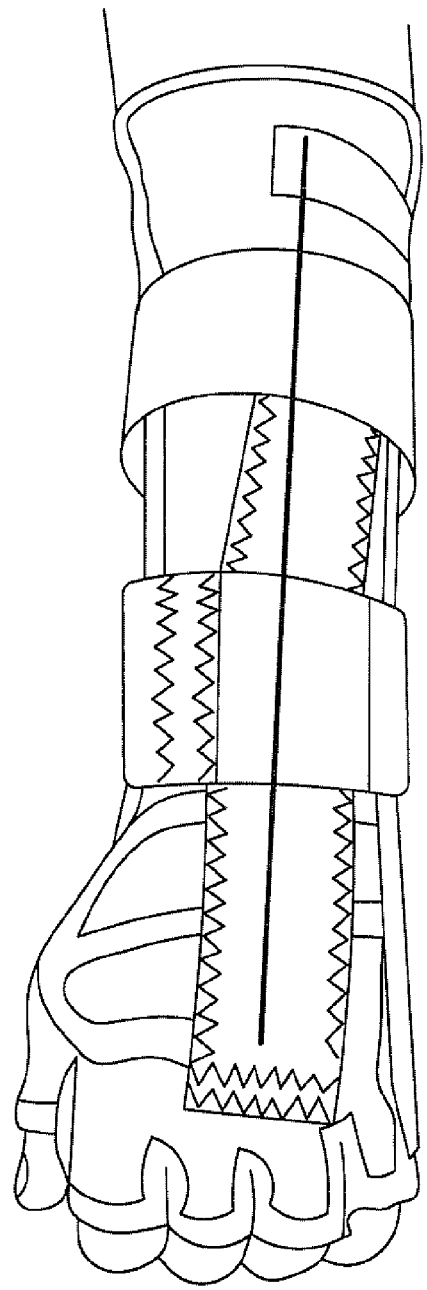

As illustrated in FIG. 11E, the patient's wrist has an abnormal ulna deviation of 10 degrees. The resilient panel 114 on the glove 110 applies a force that resists this ulna deviation and urges that patient's wrist towards a more neutral position as illustrated in FIG. 11F.

The resistive force developed by the resilient panels in any device may be determined according to the individual patient's needs. For example, a young patient may not require a glove portion that develops high resistance to correct abnormal wrist posture, whereas an adult patient may require a glove that develops a higher force. The thickness of panels, number of panels, and or material used to form the panels are among the parameters that may be altered in order to achieve a desired resistive force.

Although this specific embodiment illustrates the use of a device to treat a patient presenting abnormal flexion and ulna deviation of the wrist along with abnormal pronation of the forearm, it is clear that the invention may be utilized for the correction of other issues. For example, if the patient suffered from an abnormal extension of the wrist, resilient panels would be positions to counter this extention. Likewise, the patient may suffer from radial deviation of the wrist and/or forearm supination. Resilient panels may be positioned on the glove at suitable orientations to counteract these conditions.

Figure 12:
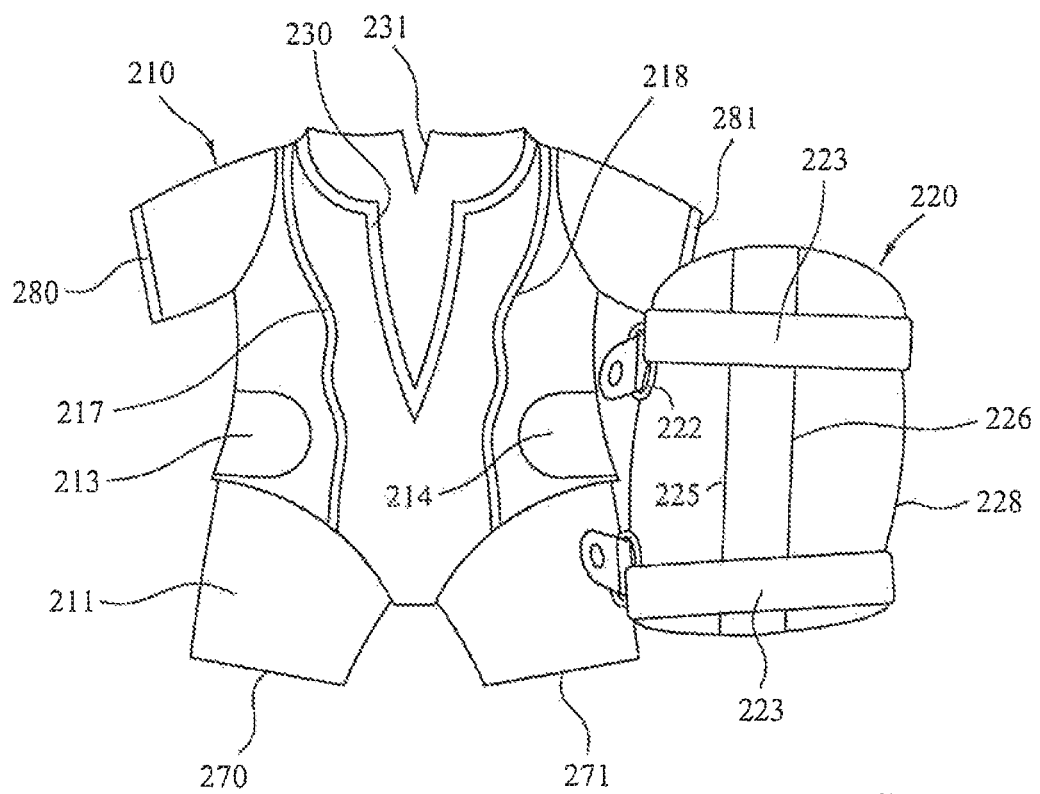
FIG. 12 illustrates a first portion and a second portion of a thoracic orthotic device according to a third embodiment of the invention.
Figure 13:
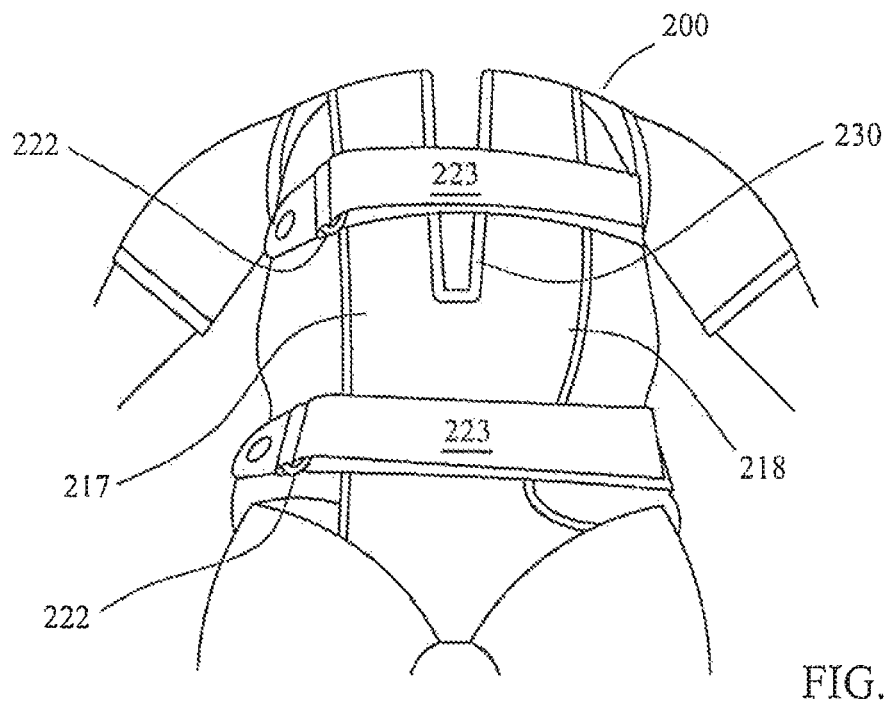
FIG. 13 illustrates a frontal view of the orthotic device according to the third embodiment of the invention, showing the first portion and the second portion in an as-coupled state.

FIGS. 12 and 13 illustrate an orthotic device according to a third embodiment of the invention. These figures show a thoracic lumbar orthosis or orthotic device 200 comprising two separate couplable portions. The first portion 210 is a dynamic elastomeric orthosis designed to conform to the torso of a patient. The second portion 220 is a rigid polyethylene thoracic brace configured to support the patient's spinal column. The elastomeric orthosis portion 210 and the rigid orthosis portion 220 are coupled together to form the orthotic device 200.

The elastomeric orthosis 210 is in the form of a body-suit constructed from a lightweight elastomeric material 211. The suit 210 has leg holes 270, 271 and arm holes 280, 281 and a zippered neck opening having front 230 and rear 231 zippers to facilitate donning of the suit. Panels of resilient material 213, 214 are sewn onto the underlying elastomeric material 211 to apply forces to the wearer's pelvis and spinal column, for example to apply compressive forces to the pelvis and to correct lateral curvature of the spinal column. The underlying material is an elastomeric material having a composition of 51% polyamide, 17% cotton and 32% DORLASTAN® material, and the resilient panels are an elastomeric material having a composition of 81% polyamide and 19% LYCRA® material.

The suit 210 defines two pockets 217, 218 for accepting a portion of the brace portion 220 of the device 200.

The thoracic brace 220 is a custom made polyethylene brace for conforming to the wearer's torso and for supporting the wearer's spinal column. The brace is formed as an anterior-opening shell, sufficiently flexible that a front portion can be opened to allow the brace to fit around the torso of a patient. The brace fastens at the patient's front.

The brace 220 further comprises a plurality of loops 222, which are affixed to the brace, and corresponding straps 223 for tightening the brace and for securing the brace in position coupled to the suit.

In use, a patient unzips the front and rear zippers 230, 231 on the suit 210 and guides his legs through the leg-holes 270, 271. The patient slides the suit up his body until the patient's front hip bone is centred into pelvis reinforcement included in the suit. Then the patient guides his arms through the arm-holes 280, 281 and the front and rear zippers 230, 231 are closed.

To couple the suit portion 210 and the brace portion 220, the patient is placed on their side. The shell of the brace is flexed to open it and then placed in position on the patient so that a waist roll 228 defined by the brace conforms to the waist roll of the patient. Left and right sides 225, 226 to the brace shell are then inserted into the pockets 217, 218 of the suit to locate the brace and the straps 223 are fastened to both tighten the brace and to couple the brace 220 to the suit 210.

Figure 13B:
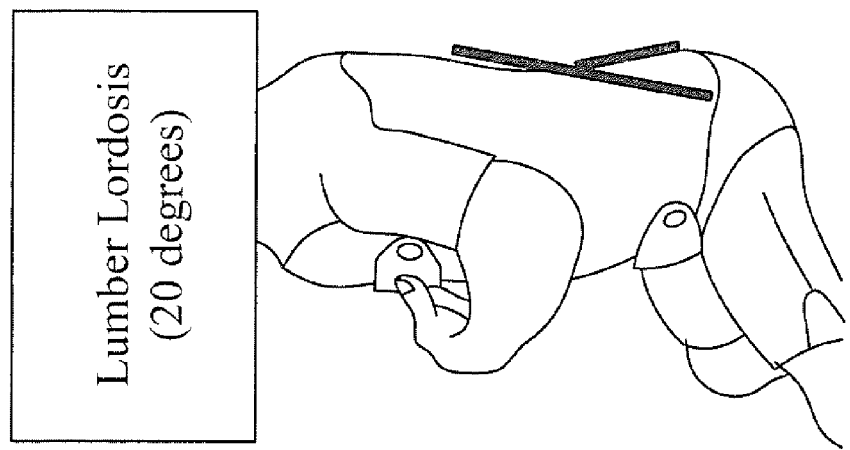
FIGS. 13A and 13B illustrate the use of the device according to the third embodiment of the invention in correcting an abnormal lumber kyphosis.
Figure 13A:
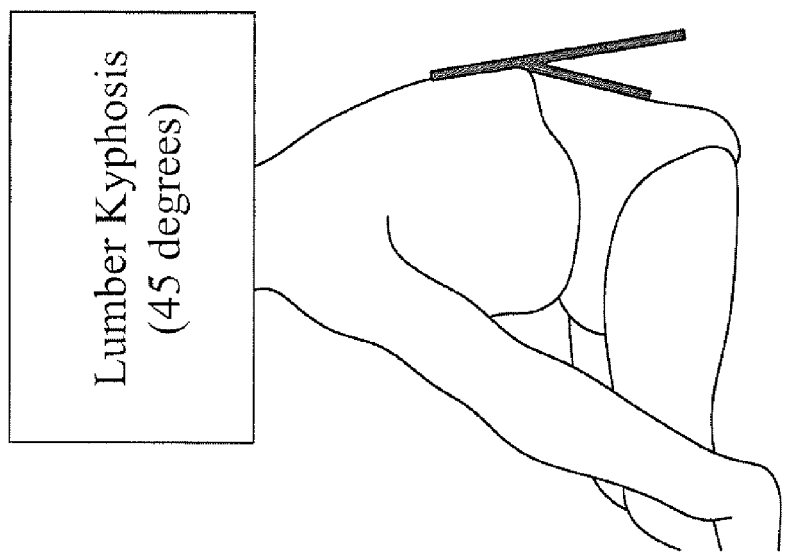

FIGS. 13A and 13B illustrate the use of an orthotic device according to a fourth embodiment of the invention. The patient illustrated in FIG. 13A has an abnormal curvature of the lower back, or lumbar kyphosis, having an angle of 45 degrees. The application of an orthotic device consisting of the suit 210 and brace 220 described above results in a 65 degree alteration in the angle of the lower spine, from a 45 degree lumbar kyphosis to a 20 degree lumber lordosis (FIG. 13B).

Figure 14:
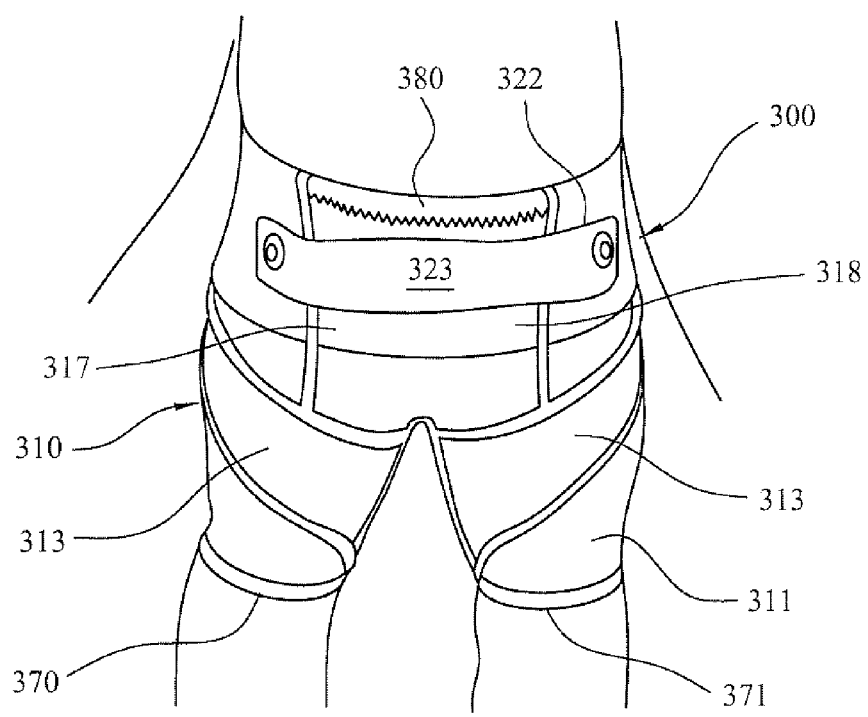
FIG. 14 illustrates a frontal view of a pelvic orthotic device according to a fourth embodiment of the invention.
Figure 15:
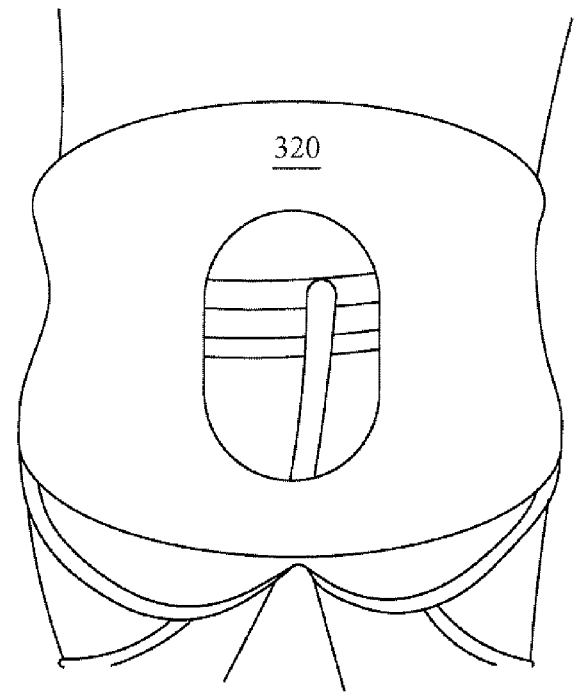
FIG. 15 illustrates a rear view of the orthotic device according to the fourth embodiment of the invention.

FIGS. 14 and 15 illustrate an orthotic device according to a fourth embodiment of the invention. These figures show a pelvic orthosis or orthotic device 300 comprising two separate couplable portions. The first portion 310 is a dynamic elastomeric orthosis designed to conform to the pelvis of a patient. The second portion 320 is a rigid polyethylene pelvic brace configured to support the patient's pelvis and lumbar spinal column. The elastomeric orthosis portion 310 and the rigid orthosis portion 320 are coupled together to form the orthotic device 300.

The elastomeric orthosis 310 is in the form of orthotic shorts constructed from a lightweight elastomeric material 311. The shorts 310 have leg holes 370, 371 and a waist opening 380 for encircling a wearer's waist. Panels of resilient material 313, 314 are sewn onto the underlying elastomeric material 311 to apply forces to the wearer's pelvis and groin, for example to apply compressive forces to the pelvis. The underlying material is an elastomeric material having a composition of 51% polyamide, 17% cotton and 32% DORLASTAN® material, and the resilient panels are an elastomeric material having a composition of 81% polyamide and 19% LYCRA® material.

The shorts 310 define two pockets 317, 318 for accepting a portion of the brace portion 320 of the device 300.

The pelvic brace 320 is a custom made polyethylene brace for conforming to the wearer's pelvis and for supporting the wearer's lower spinal column. The brace is formed as an anterior-opening shell, sufficiently flexible that a front portion can be opened to allow the brace to fit around the pelvis of a patient. The brace fastens at the patient's front.

The brace 320 further comprises a fastening loop 322, which is affixed to the brace, and a corresponding strap 323 for tightening the brace and for securing the brace in position coupled to the shorts.

In use, the shorts are donned and then the brace is positioned around the patient's waist. Left and right sides of the brace shell are then inserted into the pockets 317, 318 of the shorts to locate the brace, and the straps 323 are fastened to both tighten the brace and to couple the brace 320 to the shorts 310.

What is claimed is:

1. An orthotic device for a wearer's torso, the orthotic device being a spinal orthosis, comprising:
    a first portion comprising a suit having a resilient material for conforming to the wearer's torso, the first portion being configured to resiliently deform when worn and thereby apply a force in one or more predetermined directions to assist or restrict movement of a spinal column of the wearer's torso; and
    a second portion comprising a brace formed from rigid or semi-rigid material shaped to fit around and conform to the wearer's torso, for restricting movement of the wearer's spinal column,
    wherein the second portion is removably couplable to the first portion such that the second portion can be removed from, or coupled to, the first portion while the first portion is being worn, and
    wherein the first portion comprises a means for locating the second portion in a predetermined position with respect to the first portion.

2. An orthotic device according to any claim 1, further comprising means for coupling the first portion with the second portion, the means for coupling incorporated in the first portion, the second portion, or both.

3. An orthotic device according to claim 2, wherein the means for coupling comprises a strap, a fastener, a strap in combination with a fastener, or a fastener selected from the group comprising a hook and loop fastener, a popper, a button, a magnetic fastener, a zipper, and a buckle.

4. An orthotic device according to claim 2, wherein the means for coupling the first portion to the second portion comprises a means for location of the second portion.

5. An orthotic device according to claim 1, wherein the first portion comprises resilient means for applying the force acting in the one or more predetermined directions to assist or restrict movement of the wearer's spinal column.

6. An orthotic device according to claim 5, wherein the resilient means comprises one or more strips or panels of resilient material attached to the first portion.

7. An orthotic device according to claim 1, wherein the means for locating the second portion comprises a pocket or a slit defined in the first portion, at least part of the second portion being insertable into the pocket or slit to locate the second portion with respect to the first portion.

8. An orthotic device according to claim 7, wherein the brace comprises an anterior opening shell with a left side and a right side, and in which an anterior part of the first portion defines pockets for receiving the left and right sides of the brace.

9. An orthotic device according to claim 1, wherein the first portion is a dynamic elastomeric fabric orthosis.

10. An orthotic device according to claim 1, wherein the rigid or semi-rigid material of the second portion is a polymeric material, a composite material, or a lightweight metallic alloy.

11. An orthotic device according to claim 1, wherein the suit defines one or more pockets or slits for receiving a portion of the brace to locate the brace relative to the suit.

12. An elastomeric orthosis for use as the first portion of the orthotic device of claim 1.

13. An orthotic device according to claim 1, wherein the brace is an anterior opening shell, sufficiently flexible that a front portion of the shell can be opened to fit around the wearer's torso.

14. An orthotic device according to claim 1, wherein the suit defines leg holes, arm holes and a neck opening.

15. A method of using an orthotic device comprising a first portion comprising a suit having a resilient material and a second portion comprising a brace formed from a rigid or semi-rigid material that is shaped to fit around and conform to a wearer's torso, wherein the first portion comprises a means for locating the second portion in a predetermined position with respect to the first portion, the method comprising the steps of:
  donning the first portion on the wearer's torso so that the first portion resiliently deforms and thereby conforms to the wearer's torso and thereby applies a force in one or more predetermined directions to assist or restrict movement of a spinal column of the wearer's torso; and
  coupling the second portion to the first portion to effect rigid bracing of the wearer's spinal column for a rigid-bracing period of time.

16. A method according to claim 15, further comprising the step of uncoupling the second portion from the first portion and removing the second portion from the second portion after the rigid-bracing period of time to thereafter effect non-rigid bracing of the wearer's spinal column for a non-rigid bracing period of time.

17. A method according to claim 16, further comprising the step of, after the non-rigid bracing period of time, re-coupling the second portion to the first portion for a further rigid-bracing period of time.

18. A method according to claim 15, further comprising the step of inserting at least a portion of the second portion into a slit or pocket defined in the first portion to locate the second portion relative to the first portion.

19. A method according to claim 15, further comprising the step of releasably fastening a strap to couple the second portion to the first portion.

* * * * *